United States Patent [19]
Wood et al.

[11] Patent Number: 6,001,956
[45] Date of Patent: *Dec. 14, 1999

[54] COPOLYMERS OF POLYASPARTIC ACID AND POLYCARBOXYLIC ACIDS AND POLYAMINES

[75] Inventors: Louis L. Wood, Rockville; Gary J. Calton, Elkridge, both of Md.

[73] Assignee: Bayer AG, Germany

[*] Notice: This patent is subject to a terminal disclaimer.

[21] Appl. No.: 09/005,085

[22] Filed: Jan. 9, 1998

Related U.S. Application Data

[60] Continuation of application No. 08/421,485, Apr. 13, 1995, Pat. No. 5,708,126, which is a division of application No. 07/994,922, Dec. 22, 1992, Pat. No. 5,408,028.

[51] Int. Cl.$^6$ .............................. C08G 69/10; C08G 73/00
[52] U.S. Cl. ......................... 528/328; 528/363; 525/419; 525/420
[58] Field of Search ...................... 528/328, 363; 525/419, 420

[56] References Cited

U.S. PATENT DOCUMENTS

| | | | |
|---|---|---|---|
| 2,306,918 | 12/1942 | Weiss et al. | 260/78 |
| 3,052,655 | 9/1962 | Fox et al. | 260/78 |
| 3,351,520 | 11/1967 | Spicer et al. | 162/164 |
| 3,846,380 | 11/1974 | Fujimoto et al. | 260/78 A |
| 4,169,924 | 10/1979 | Barabas et al. | 525/377 |
| 4,363,797 | 12/1982 | Jacquet et al. | 424/70 |
| 4,839,461 | 6/1989 | Boehmke | 528/363 |
| 4,996,292 | 2/1991 | Fox et al. | 528/328 |
| 5,057,597 | 10/1991 | Koskan | 528/328 |
| 5,152,902 | 10/1992 | Koskan et al. | 210/698 |
| 5,219,952 | 6/1993 | Koskan et al. | 525/419 |
| 5,266,237 | 11/1993 | Freeman et al. | 252/542 |
| 5,266,305 | 11/1993 | Wood et al. | 425/54 |
| 5,286,810 | 2/1994 | Wood | 525/421 |
| 5,288,783 | 2/1994 | Wood | 525/418 |
| 5,296,578 | 3/1994 | Koskan et al. | 528/363 |
| 5,306,429 | 4/1994 | Wood et al. | 210/698 |
| 5,319,145 | 6/1994 | Paik et al. | 528/328 |
| 5,328,631 | 7/1994 | Du Vosel et al. | 252/174.23 |
| 5,357,004 | 10/1994 | Calton et al. | 525/435 |
| 5,371,179 | 12/1994 | Paik et al. | 528/363 |
| 5,391,642 | 2/1995 | Wood | 525/435 |
| 5,393,868 | 2/1995 | Freeman et al. | 528/480 |
| 5,408,028 | 4/1995 | Wood et al. | 528/328 |
| 5,442,038 | 8/1995 | Wood et al. | 528/363 |
| 5,484,860 | 1/1996 | Wood et al. | 525/432 |
| 5,494,995 | 2/1996 | Wood et al. | 528/328 |
| 5,519,110 | 5/1996 | Wood et al. | 528/363 |
| 5,521,279 | 5/1996 | Wood et al. | 528/363 |
| 5,552,518 | 9/1996 | Wood et al. | 528/363 |
| 5,708,126 | 1/1998 | Wood et al. | 528/328 |

FOREIGN PATENT DOCUMENTS

| | | |
|---|---|---|
| B-40155/93 | 1/1994 | Australia . |
| B-63034/94 | 11/1994 | Australia . |

*Primary Examiner*—P. Hampton-Hightower
*Attorney, Agent, or Firm*—Connolly, Bove, Lodge & Hutz LLP

[57] ABSTRACT

Copolymers of polyaspartic acid which are suitable for the inhibition of scale deposition were obtained by reacting maleic acid, an additional polycarboxylic acid and ammonia in a stoichiometric excess, at 120°–350° C., preferably 180°–300° C., to provide copolymers of polysuccinimide. In a second embodiment, a polyamine was added to the reaction mix. These intermediate polysuccinimide copolymers could then be converted to the salts of copolymers of polyaspartic acid by hydrolysis with a hydroxide. Such copolymers are useful in preventing deposition of scale from water and find applications in treating water. Other applications include scale prevention additives for detergents. In addition, such copolymers inhibit dental tartar and plaque formation.

4 Claims, No Drawings

COPOLYMERS OF POLYASPARTIC ACID AND POLYCARBOXYLIC ACIDS AND POLYAMINES

This application is a continuation of application Ser. No. 08/421,485, filed on Apr. 13, 1995, which issued to U.S. Pat. No. 5,708,126 on Jan. 13, 1988, which in turn was a divisional of U.S. patent application Ser. No. 07/994,922, filed on Dec. 22, 1992, now U.S. Pat. No. 5,408,028. The entire disclosures of U.S. patent application Ser. Nos. 08/421,485 and 07/994,922 as originally filed are hereby expressly incorporated by reference in the present continuation application.

FIELD OF THE INVENTION

This invention relates to a process for the production of copolymers of polysuccinimide, their conversion to salts of copolymers of polyaspartic acid and the use of these materials.

BACKGROUND OF THE INVENTION

Polyaspartic acid is a peptide chain in which amide linkages extend the chain. In the thermal polymerization of aspartic acid, the stereochemistry of the aspartic acid is racemized and the formation of both $\alpha$ and $\beta$ carboxylic acid groups have the ability to react to form such amide bonds. Such materials have been used for fertilizers and scale inhibition agents. They are particularly useful for the prevention of scale deposition in boiler water, reverse osmosis membranes, detergents and as inhibitors of dental tartar and plaque formation (tartar barrier agents). These materials are readily biodegradable. Methods for the preparation of polyaspartic acid have been developed (See U.S. Pat. Nos. 5,057,597 and 4,839,461 and U.S. patent application Ser. No. 07/882,919, filed May 14, 1992, Louis L. Wood, and U.S. patent application Ser. No. 07/926,242, filed Aug. 7, 1992, Louis L. Wood).

Biodegradability, calcium ion exchange ability and the disruption of calcium salt crystal structure are important properties of materials used in the prevention of scale deposition in boiler water, on reverse osmosis membranes, in detergent use and as inhibitors of dental tartar and plaque formation (tartar barrier agents). We searched for economically useful materials, having a greater retention on the object wherein inhibition of scale deposition is desired. Other desirable properties were greater stability to biodegradation in addition to intrinsic value for the prevention of scale deposition in boiler water, on reverse osmosis membranes, during detergent use and as inhibitors of dental tartar and plaque formation (tartar barrier agents). We have found that the addition of polycarboxylic acids in the thermal polymerization of maleic acid or aspartic acid produced novel and highly effective copolymers which possessed these properties.

DESCRIPTION OF RELATED ART

A number of methods of preparation of polyaspartic acid are disclosed in the literature and other patents, however, no mention is made of methods of preparation of copolymers of polysuccinimide and polycarboxylic acids which may then be converted to copolymers of polyaspartic acid and polycarboxylic acids.

SUMMARY OF THE INVENTION

Copolymers of polysuccinimide were prepared by reacting maleic acid, ammonia and a polycarboxylic acid at temperatures greater than 120° C. These copolymers could be converted to copolymers of polyaspartic acid by addition of a hydroxide.

In a second embodiment of the invention, copolymers of polysuccinimide were prepared by reacting maleic acid, ammonia, a polycarboxylic acid and a polyamine at temperatures greater than 120° C. These copolymers could be converted to copolymers of polyaspartic acid by addition of a hydroxide.

One object of this Invention is to provide a means of preparing copolymers of polysuccinimide. A further object of this invention is to provide a means of preparing copolymers of polyaspartic acid. Yet another object of this invention is to provide novel compositions which are useful for the inhibition of salt deposition, especially bivalent metal salts, whether in water treatment, detergent addition, oral health care or cosmetic formulation. Yet another object of this Invention is to provide novel compositions which may be further reacted to provide useful compounds for water treatment, cosmetics, oral health care and detergents.

DETAILED DESCRIPTION OF THE EMBODIMENTS

Copolymers of polyaspartic acid which are suitable for the inhibition of scale deposition may be obtained by reacting maleic acid, an additional polycarboxylic acid and ammonia in a stoichiometric excess, at 120°–350° C., preferably 180°–300° C., and then converting the copolymer of polysuccinimide formed to a salt of a copolymer of polyaspartic acid by hydrolysis with a hydroxide.

In a second embodiment, copolymers of polyaspartic acid which are suitable for the inhibition of scale deposition may be obtained by reacting maleic acid, an additional polycarboxylic acid, ammonia in a stoichiometric excess, and a compound having 2 or more primary or secondary amine groups per molecule, at 120°–350° C., preferably 180°–300° C., and then converting the copolymer of polysuccinimide formed to a salt of a copolymer of polyaspartic acid by hydrolysis with a hydroxide.

The reaction is carried out first by the addition of water to maleic anhydride, thus forming maleic acid, or to maleic acid itself, and the polycarboxylic acid, followed by addition of the appropriate amount of ammonia in the form of gaseous ammonia or as its aqueous solution. At this point, the polyamine may be added to either of these alternative embodiments. This solution is then heated to remove water. As water is removed, the mixture becomes a solid and then a melt of the mixture is formed. Water removal continues as the reaction proceeds and the temperature is brought to 120°–300° C. When the theoretical quantity of water formed in the production of the copolymer of polysuccinimide has been removed, which, depending on the temperature, may occur in even less than 5 minutes, the reaction mixture is allowed to cool. Typically, it may take over 4 hours at 120° C., whereas it may take less than 5 minutes at 300° C. The copolymer of polysuccinimide formed can be used to make other novel and useful products by reactions such as those described in U.S. Pat. No. 4,363,797 or U.S. Pat. No. 3,486,380, wherein useful derivatives for cosmetic use are described. The copolymers of polysuccinimide can also undergo alkaline hydrolysis to provide the appropriate salt of a copolymer of polyaspartic acid. Further manipulation to remove the water or the salts can be carried out to provide water free powders of the salts or the free acid.

The polyamines which may be used to produce these copolymers of this invention have been described in U.S.

patent application Ser. No. 07/926,242, filed Aug. 7, 1992, Louis L. Wood, incorporated herein by reference, are amines which have at least two or more primary or secondary amines available for reaction. Preferred polyamines have at least two primary amine groups. The concentration may range from greater than 0 to 50%, however, the preferred range is greater than 0 to 30%.

Any aliphatic or aromatic polycarboxylic acid may be used in this invention, but the preferred acids are adipic acid, citric acid, fumaric acid, malic acid, malonic acid, succinic acid, glutaric acid, oxalic acid, pimelic acid, itaconic acid, nonanedioic acid, dodecanedioic acid, octanedioic acid, isophthalic, terphthalic and phthalic acid. The concentration may range from greater than 0 to 50%, however, the preferred range is greater than 0 to 30%.

The hydroxides useful in converting the copolymers of polysuccinimide formed above to copolymers of polyaspartic acid include, but are not limited to, the alkali and alkaline earth metals and ammonia, examples of which as their cations are, $Na^+$, $K^+$, $Mg^+$, $Li^+$, and $Ca^{++}$, $Zn^{++}$, $Ba^{++}$, $Co^{++}$, $Fe^{++}$, $Fe^{+++}$, and $NH_4^+$.

Polysuccinimide is the imide form of polyaspartic acid and is also known as anhydropolyaspartic acid.

The term "succinimide" is understood in the art to include many of the amide, imide and amidine species which are also formed by this reaction. The predominant product however is succinimide and this term is used to refer to the thermally polymerized reaction product of maleic acid and ammonia or a polyamine. The polyaspartic moieties formed by hydrolysis of the polysuccinimides formed would be principally α and β aspartates.

The copolymers of polyaspartic acid provided by the present invention are advantageous for inhibition of scale deposition in water treatment, as detergent additives, in oral health care or in cosmetic formulation. Solutions of the salts of copolymers of polyaspartic acid formed in this manner have excellent scale inhibition performance. Salts which may be inhibited are the salts of Mg, Ca, Sr, Ba, and Ra. The carbonate, sulfate and phosphate salts are those in which greatest inhibition is shown.

The following examples are by way of illustration and not by way of limitation.

EXAMPLE 1
Preparation of a Polyaspartic Acid/Citric Acid Copolymer

A slurry of 19.6 g (0.2 mole) maleic anhydride was dissolved in 40 ml water at 80°–95° C. and 4.2 g (0.02 moles) of citric acid monohydrate (Formula weight 210) was added and the mixture was stirred until all solids were in solution, after which the mixture was allowed to cool to 25° C. To this solution at 25° C. was added 60 g of 30% aqueous solution of ammonium hydroxide (0.44 mol $NH_3$). This solution was evaporated to dryness over a period of 8 minutes. The solid was then heated at 235°–245° C. for 5 minutes, removed from the heat, allowed to cool and broken up with a spatula. The solid was then heated at 235°–245° C. for a second 10 minute period, removed from the heat, allowed to cool and broken up with a spatula. Finally, the solid was heated at 235°–245° C. for a third 10 minute period, removed from the heat and allowed to cool to room temperature. The resulting water insoluble copolymer of polysuccinimide and citric acid (21.7 g) was slurried in 29.1 ml of water and a solution of 8.0 g of sodium hydroxide in 12 ml of water was added over 5 minutes. The solution was stirred for 10–20 minutes to give a clear red-brown solution of a copolymer of polyaspartic acid and citric acid.

EXAMPLE 2
Preparation of a Polyaspartic Acid/Succinic Acid Copolymer

A slurry of 19.6 g (0.2 mole) maleic anhydride was dissolved in 40 ml water at 80°–95° C. and 2 g (0.02 moles) of succinic anhydride (Formula weight 100) was added and the mixture was stirred until all solids were in solution, after which the mixture was allowed to cool to 25° C. To this solution at 25° C. was added 60 g of 30% aqueous solution of ammonium hydroxide (0.44 mol $NH_3$). This solution was evaporated to dryness over a period of 8 minutes. The solid was then heated at 235°–245° C. for 5 minutes, removed from the heat, allowed to cool and broken up with a spatula. The solid was then heated at 235°–245° C. for a second 10 minute period, removed from the heat, allowed to cool and broken up with a spatula. Finally, the solid was heated at 235°–245° C. for a third 10 minute period, removed from the heat and allowed to cool to room temperature. The resulting water insoluble copolymer of polysuccinimide and succinic acid (21.9 g) was slurried in 29.1 ml of water and a solution of 8.0 g of sodium hydroxide in 12 ml of water was added over 5 minutes. The solution was stirred for 10–20 minutes to give a clear red-brown solution of a copolymer of polyaspartic acid and succinic acid.

EXAMPLE 3
Precipitation Assay for Calcium Sulfate

The material to be tested as an inhibitor of scale formation was added in appropriate quantities to a solution of 5 ml of calcium chloride solutions (21.6 g/L of $CaCl_2$ dihydrate and 41.4 g/L of NaCl) and 5 ml of sulfate solution (20.9 g/L of $Na_2SO_4$ and 41.4 g NaCl). The mixture was then placed in an oven at 160° F. for 3 hours. Finally the mixture was filtered through Whatman #2 paper and dried at 160° F. for 8 hours, after which the weight of precipitate was determined.

The polycarboxylic acid/polyaspartic acid copolymers were tested in the above assay. The results are given below in Table 1.

TABLE 1

| compound | polycarboxylic acid | weight of precipitate (mg) |
| --- | --- | --- |
| blank | | 44 |
| polyacrylate, 5000 molecular weight | | 46 |
| copolymer polyaspartate/citrate | citric acid | 16 |
| copolymer polyaspartate/succinate | succinic acid | 13 |

The copolymers of polyaspartic acid and polycarboxylic acids were very effective agents for the inhibition of mineral scale.

EXAMPLE 4
Calcium Oxalate Titration

A 0.25 g sample of the sodium salt of the polyaspartic/citric acid copolymer prepared in Example 1 was placed in a beaker with 100 ml of deionized water and 1 ml of 3% sodium oxalate was added. The solution was titrated with 0.1 mol of calcium chloride till the slurry turned white.

Duplicate samples gave values of 6.4 and 6.6 ml. Sodium tripolyphosphate gave required 8.2 and 8.1 ml while a polyaspartic acid prepared from diammonium maleate required 8.3 and 8.5 ml. This shows that polycarboxylic acid copolymers of polyaspartic acid are effective calcium chelators.

EXAMPLE 5
Preparation of a Polyaspartic/Citric Acid Copolymer with a Polyamine A solution of 2.1 g (0.01 moles) of citric acid monohydrate (Formula weight 210) and 0.32 g (0.0028 moles) hexanediamine was added to 19.6 g (0.2 mole) maleic anhydride which had been dissolved in 40 ml water at 80°–95° C., and finally 30 g of 30% aqueous solution of ammonium hydroxide (0.22 mol $NH_3$) was added. This solution was evaporated to dryness over a period of 30 minutes. The solid was then heated at 195°–220° C. for 10 minutes, removed from the heat, allowed to cool and broken up with a spatula. The solid was then heated at 230°–245° C. for 10 minutes, removed from the heat, allowed to cool and broken up with a spatula Finally, the solid was heated at 230°–245° C. for 10–15 minutes, removed from the heat and allowed to cool to room temperature. The resulting water insoluble polymer was slurried in 40.0 ml of water and a solution of 8.0 g of sodium hydroxide in 12 ml of water was added over 5 minutes. The solution was stirred for 10–20 minutes to give a clear red-brown solution, pH 10–11.0 of a copolymer of polyaspartic acid, citric acid and hexanediamine. The tests for $CaSO_4$, Example 3, and $CaCO_3$ (below) were run and the result are recorded in Table 2.

Inhibition of Calcium Carbonate Precipitation by the Calcium Drift Assay

In this assay a supersaturated solution of calcium carbonate is formed by adding 29.1 ml of 0.55 M NaCl and 0.01 M KCl to 0.15 ml of 1.0 M $CaCl_2$ and 0.3 ml of 0.5 M $NaHCO_3$. The reaction is initiated by adjusting the pH to 7.5–8.0 by titration with 1 N NaOH and addition of the material to be tested for inhibition of $CaCO_3$ precipitation at a level of 1.7 ppm. At three minutes, 10 mg of $CaCO_3$ is added and the pH is recorded. The decrease in pH is directly correlated to the amount of $CaCO_3$ that precipitates.

TABLE 2

| Sample | $CaSO_4$ ppt (mg) | $CaCO_3$ Drift (pH units) |
| --- | --- | --- |
| none | 84 | .72 |
| copolymer | 74 | .26 |

These assays indicate that the copolymer of Example 5 is effective in prevention of $CaSO_4$ and $CaCO_3$ scale.

The following examples will serve to illustrate the tartar barrier compositions of this invention. Copolymers of Examples 1, 2 and 5 are suitable tartar barrier agents. Humectants are materials such as glycerol, Foaming agents are suitable surfactants. Sweetening agents may be normal or artificial sweeteners. Common abrasives are materials like fumed silica. Gelling agents are polymers which are used to prepare thickened solutions.

| | % w/w |
| --- | --- |
| EXAMPLE A — Mouthwash | |
| Tartar barrier agent | 0.5–2 |
| humectant | 6.0 |
| foaming agent | 1.0 |
| sweetener | 0.3 |
| deionized water | q.s. to 100 |
| flavors | 1.0 |
| EXAMPLE B — Abrasive Dentrifice Gel | |
| Tartar barrier agent | 2–10 |
| detergent | 1.5 |
| humectant | 10.0 |
| sweetener | 0.2 |
| deionized water | q.s. to 100 |
| flavors | 1.0 |
| abrasive | 55.0 |
| gelling agent | 2.0 |
| EXAMPLE C — Chewing gum | |
| Tartar barrier agent | 1.0–11 |
| Gum base | 21.3 |
| sugar | 48.5–58.5 |
| corn syrup | 18.2 |
| flavors | 1 |

It will be apparent to those skilled in the art that the examples and embodiments described herein are by way of illustration and not of limitation, and that other examples may be utilized without departing from the spirit and scope of the present invention, as set forth in the appended claims.

We claim:

1. A copolymer of polyaspartic acid, a polycarboxylic acid and a polyamine.

2. The copolymer of claim 1 wherein the polyamine has at least one primary amine and wherein the additional amine group or groups consist of at least one primary or secondary amine.

3. The copolymer of claim 2 wherein the polyamine is selected from the group consisting of diethylene triamine, a polyoxyalkyleneamine diamine or triamine, melamine, an alkyl diamine or triamine, ethylene diamine and hexanediamine.

4. The copolymer of claim 1 wherein the polycarboxylic acid is selected from the group consisting of adipic acid, citric acid, fumaric acid, malic acid, malonic acid, succinic acid, glutaric acid, oxalic acid, pimelic acid, itaconic acid, nonanedioic acid, dodecanedioic acid, octanedioic acid, isophthalic, terphthalic and phthalic acid.

* * * * *